(12) United States Patent
Ye et al.

(10) Patent No.: US 8,524,469 B2
(45) Date of Patent: Sep. 3, 2013

(54) TWO-STEP GRAM STAINING METHOD

(75) Inventors: Ying Ye, Shanghai (CN); Tao Yuan, Shanghai (CN); Li-Xin Yang, Shanghai (CN); Feng-Qi Wen, Shanghai (CN)

(73) Assignee: Ying Ye, Shanghai (CN)

( * ) Notice: Subject to any disclaimer, the term of this patent is extended or adjusted under 35 U.S.C. 154(b) by 1079 days.

(21) Appl. No.: 12/130,456

(22) Filed: May 30, 2008

(65) Prior Publication Data

US 2009/0042242 A1      Feb. 12, 2009

(30) Foreign Application Priority Data

Aug. 7, 2007   (CN) .......................... 2007 1 0044663

(51) Int. Cl.
*G01N 1/30*     (2006.01)
*C12Q 1/04*     (2006.01)

(52) U.S. Cl.
USPC .......................................... 435/40.5; 435/34

(58) Field of Classification Search
USPC .................................................. 435/34, 40.5
See application file for complete search history.

(56) References Cited

PUBLICATIONS

Kibota. 2010. Lab Module 6—Gram-Staining. downloaded from http://web.clark.edu/tkibota/240/Lab/LM6_GramStain/GramStain.pdf. p. 1-3.*

* cited by examiner

*Primary Examiner* — Taeyoon Kim
(74) *Attorney, Agent, or Firm* — Muncy, Geissler, Olds & Lowe, PLLC

(57) ABSTRACT

The present invention provides a two-step Gram staining method. The method is conducted by using a clean slide, followed by adding 10~30 μl primary stain from a reagent kit, adding an equivalent amount of specimens uniformly on said slide, then immediately adding 30~60 μl counter-stain on said slide for incubating 15 seconds, rinsing with water, and finally examining under a microscope, the result appears color contrast on the center of the slide between the Gram-negative bacteria performing light red color and the Gram-positive bacteria performing deep purple color.

5 Claims, No Drawings

TWO-STEP GRAM STAINING METHOD

FIELD OF THE INVENTION

The present invention relates to a Gram staining method, and more particular to a two-step Gram staining method.

BACKGROUND OF THE INVENTION

The Gram staining method is one of the widely used differential staining methods in bacteriology, established by the Danish doctor, Hans Christian Gram, in 1884. The bacteria first were stained by the basic primary stain, followed by the addition of a mordant (Gram's iodine), and then decolorized with ethyl alcohol. Some of the bacteria remain their stain color without decolorization in certain conditions, while some are decolorized. Therefore the bacteria can be classified into two groups, the former is Gram-positive (G+) bacteria and the latter is Gram-negative (G−) bacteria. For clear observation, a final step of counter-staining with safranin or basic fuchsin is applied after decolorization. The color of Gram-positive remains purple while the Gram-negative bacteria were stained to appear red. The Gram-positive bacteria include *Bacillus*, most of the coccus such as *Staphylococcus, Streptococcus, Enterococcus*, and all of the actinobacteria and the eubacteria. The Gram-negative bacteria include *Vibrio, Spirochaeta* and Bacteria.

The Gram-positive bacteria and the Gram-negative bacteria turn up differently on their chemical, physical properties and their staining results as well. Currently, it is generally acknowledged that the Gram-positive bacteria have unique complexes of nucleoprotein magnesium salt and polysaccharide, and the combinations between the complexes of the Gram-positive bacteria and the complexes of crystal violet and iodine (CV-I) within the inner and outer layers of the cell are strong, therefore the Gram-positive bacteria are not easy to be decolorized. In the contrast, the combinations between the complexes of the Gram-negative bacteria and the complexes of crystal violet and iodine (CV-I) within the inner and outer layers of the cell are not so strong, it causes that the Gram-negative bacteria can not absorb stains efficiently so that they can be decolorized easily. Generally, the staining mechanism is based on above principle.

Besides, the isoelectric point of the Gram-positive bacteria is much lower than the isoelectric point of the Gram-negative bacteria, so the Gram-positive bacteria can absorb many stains and be much difficult to be decolorized, while the Gram-negative bacteria are opposite under the same PH condition. Therefore, the staining conditions need to be controlled strictly. For example, in the strong base condition to progress staining, both types of the Gram-positive bacteria and the Gram-negative bacteria can absorb basic stains, therefore, it results in the positive reaction. While under the low PH condition, both of them appear the negative result. Moreover, the penetrations between the crystal violet-iodine complex and the cell walls of these two types of bacteria are not the same. The Gram-positive bacteria have lower penetration so that they are not easy to be decolorized. The Gram-negative bacteria have higher penetration so they can be easily decolorized. Therefore, the time and method for decoloriztion should be controlled strictly.

Gram Staining Mechanism:

Gram-positive bacteria have thick mesh-like cell walls made of peptidoglycan to form penetration barriers. During decolorization by the ethyl alcohol, the thicker Gram-positive cell walls dehydrate so as to close the pores as the cell walls shrink. As a result, the crystal violet-iodine complexes are blocked on the cell walls, and the bacteria remain stained and appear purple. In contrast, the Gram-negative bacteria are those bacteria having thinner layer of peptidoglycan, much loose linkage. Using ethyl alcohol to decolorize can not shirk the structure of bacteria anymore. Also, the Gram-negative bacteria contain a much higher amount of lipids, and ethyl alcohol can dissolve the lipids and increase the pores so the crystal violet-iodine complexes can be removed from the cell walls. After, a counterstain (commonly safranin) colors all Gram-negative bacteria a red color.

The Gram stain method generally includes four basic steps of applying a primary stain (crystal violet), a mordant (Gram's iodine), decolorization, and counter-staining. The specific operation includes the following steps of:

1) applying the bacteria to a slide and affixing the slide;
2) staining the bacteria with ammonium oxalate crystal violet for 1 min;
3) rinsing with water;
4) treating the slide with the mordant solvent and then waiting for 1 min;
5) rinsing the slide with water and using water-absorbing paper to absorb the extra moisture;
6) adding drops of 95% ethyl alcohol and slightly shaking to progress decolorizing for 30 seconds, rinsing with water, drying it; and
7) counter-staining the slide with safranin for 10 seconds, rinsing with water, drying it and examining with a microscope.

The result appears that Gram-positive cells remain purple while the Gram-negative cells turn to red.

The four-steps Gram staining method has great result but the operation steps are much more complicated. Owing to the busy lab working, each technique is required to be much simpler and more efficient in order to accomplish more tasks in such limited time.

In view of the drawbacks of the prior art, the inventor of the present invention based on years of experience conducted extensive researches and experiments, and finally developed a two-step gram staining method to overcome the drawbacks of the prior art.

SUMMARY OF THE INVENTION

Accordingly, the object of the present invention is to provide a two-step Gram staining method with easy operation, reliable method, stable property, and the staining result is easy to conduct and determine, in order to overcome the drawbacks of the prior art.

To achieve the foregoing object, the present invention provides a two-step Gram staining method. The method is conducted by using a clean slide, followed by adding 10~30 µl primary stain from a reagent kit, adding an equivalent amount of specimens uniformly on said slide, then immediately adding 30~60 µl counter-stain on said slide for incubating 10-20 seconds, preferably 15 seconds, rinsing with water, and finally examining under a microscope, the result appears color contrast on the center of the slide between the Gram-negative bacteria performing light red color and the Gram-positive bacteria performing deep purple color.

The primary stain can consist of 0.2 to 0.5 wt. % crystal violet, and 4 to 6 wt. % sodium chloride solvent, the preferred primary stain consists of 0.25 wt. % crystal violet and 5 wt. % sodium chloride solvent.

The counter-stain can consist of 0.2 to 0.5 wt. % basic fuchsin, 0.1 to 0.3 wt. % potassium iodide, 0.05 to 0.15 wt. % iodine and 90 to 96 wt. % ethyl alcohol, the preferred counterstain consists of 0.25 wt. % basic fuchsin, 0.2 wt. % potassium iodide and 0.1 wt. % iodine and 95 wt. % ethyl alcohol.

The reagent kit is provided with a flushing bottle. A lip of the reagent kit can be turned over to serve as a staining shelf and a container for receiving the flushing water.

Preferably, the specimen includes bacterial cultures and secretions

Compared with the conventional Gram staining method, the present invention provide a two-step Gram staining method and a reagent kit, based on the principle of the conventional four-steps Gram staining method with technique improvement, therefore, the present invention is a new staining method. With the same result of using conventional Gram staining method, the use of the new staining method and the reagent kit can progress the Gram staining and provide a faster and easier operation with lower cost and no environmental pollution. The two-step Gram staining method and the reagent kit also have the important perspective in its practical application and market. No similar patents were founded in the world so far. The present invention has the advantages in simple operation, reliable method, stable property, easy observation and determination and benefits not only for the operation of biological or medical treatment, but also for the transportation of product and being safe and reliable as well. If the present invention is conducted as a commercial product and maintained its application, the potential market is expected and can create the beneficial result in both our community and economy.

BRIEF DESCRIPTION OF THE DRAWINGS

None

DETAILED DESCRIPTION OF THE PREFERRED EMBODIMENTS

The foregoing method and other objects, features and advantages of the present invention will be better understood from the following detailed description taken with the accompanying samples.

The purpose of this invention is to overcome the unseen likely product in nations of the world, and provide a more scientific, more environmental protecting, more convenient and more human Gram staining tool. The purpose of this invention can be accomplished through the following technique.
1. The two-step Gram staining method in accordance with the present invention is different from the conventional four-step Gram staining method, which is the most important key in this invention.
2. The two reagent of an A stain (first stain or primary stain) and a B stain (second stain or counter-stain) can replace the conventional four reagent of crystal violet, Gram's iodine, decolorizer and counter-stain.
3. The reagent kit in accordance with the present invention is provided with a flushing bottle. Therefore, during the staining, the user can put the lip on the outer packing of the reagent kit, and the flushing bottle can be served as a staining shelf and a container for receiving the flushing water, so it will not cause overflowing and environmental pollution.
4. The two-step Gram staining method and reagent kit in accordance with the present invention has the advantage in using fewer amount of stains (½ to ⅓ from original usage amount) and can be operated without water flowing, so it can be applied as portable using.

Example 1

A clean slide is provided and a drop of an A reagent (first stain or primary stain) consisted of 0.25 wt. % crystal violet and 5 wt. % sodium chloride solvent, in an amount of around 10~30 μl is added on the slide. An equivalent amount of specimens, bacterial cultures, is then added to the slide and coated uniformly without further drying, and a B reagent (secondary stain or counter-stain) consisted of 0.25 wt. % basic fuchsin, 0.2 wt. % potassium iodide and 0.1 wt. % iodine and 95 wt. % ethyl alcohol is then added to cover the specimens in an amount of around 30~60 μl for incubating 15 seconds immediately. After being rinsed with water, the slide is examined under a microscope. The staining result on the center of the slide appears color contrast between the Gram-negative bacteria performing light red and the Gram-positive bacteria performing deep purple.

Example 2

A clean slide is provided and a drop of an A reagent (first stain or primary stain) consisted of 0.2 wt. % crystal violet and 4 wt. % sodium chloride solvent, in an amount of around 30 μl is added on the slide. An equivalent amount of specimens, bacterial cultures, is then added to the slide and coated uniformly without further drying, and a B reagent (secondary stain or counter-stain) consisted of 0.2 wt. % basic fuchsin, 0.1 wt. % potassium iodide and 0.05 wt. % iodine and 90 wt. % ethyl alcohol is then added to cover the specimens in an amount of around 60 μl for incubating 30 seconds immediately. Following by the steps of rinsing with water, the slide is examined under a microscope. The staining result on the center of the slide appears color contrast between the Gram-negative bacteria performing light red and the Gram-positive bacteria performing deep purple.

Example 3

A clean slide is provided and a drop of an A reagent (first stain or primary stain) consisted of 0.5 wt. % crystal violet and 6 wt. % sodium chloride solvent, in an amount of around 30 μl is added on the slide. An equivalent amount of specimens, bacterial cultures, is then added to the slide and coated uniformly without further drying, and a B reagent (secondary stain or counter-stain) consisted of 0.5 wt. % basic fuchsin, 0.3 wt. % potassium iodide and 0.15 wt. % iodine and 96 wt. % ethyl alcohol is then added to cover the specimens in an amount of around 60 μl for incubating 30 seconds immediately. After being rinsed with water, the slide is examined under a microscope. The staining result on the center of the slide appears color contrast between the Gram-negative bacteria performing light red and the Gram-positive bacteria performing deep purple.

While the invention has been described in terms of specific examples of the present invention, it is not limited to such detail since numerous modifications and variations could be made thereto by those skilled in the art without departing from the scope and spirit of the present invention. Therefore, the features and advantages of the present invention will be set forth in the claims.

What is claimed is:

1. A Gram staining method, consisting of a primary staining step and a counter-staining step, and the primary staining step and the counter-staining step further comprising the sub-steps of:
adding 10~30 μl primary stain obtained from a reagent kit on a clean slide;

adding specimens, volume of which is equivalent to said primary stain and coating uniformly on said slide, wherein said specimens include Gram-negative bacteria and Gram-positive bacteria;

adding 30~60 μl counter-stain on said slide for incubating 10~20 seconds immediately;

rinsing said slide with water and then drying said slide; and examining said slide under a microscope, wherein results appear that color contrast is present on the center of the slide in between said Gram-negative bacteria performing light red color and said Gram-positive bacteria performing deep purple color;

wherein said primary stain consists of 0.2 to 0.5 wt. % crystal violet, and 4 to 6 wt. % sodium chloride solvent, and said counter-stain consists of 0.2 to 0.5 wt. % basic fuchsin, 0.1 to 0.3 wt. % potassium iodide, 0.05 to 0.15 wt. % iodine and 90 to 96 wt. % ethyl alcohol.

2. The Gram staining method of claim 1, wherein the primary stain consists of 0.25 wt. % crystal violet and 5 wt. % sodium chloride solvent.

3. The Gram staining method of claim 1, wherein the counter-stain consists of 0.25 wt. % basic fuchsin, 0.2 wt. % potassium iodide, 0.1 wt. % iodine and 95 wt. % ethyl alcohol.

4. The Gram staining method of claim 1, further comprising a step of providing a flushing bottle included in the reagent kit, wherein the reagent kit is placed in a container, a lip of the container is able to be turned over to serve as a staining shelf and be used for receiving flushing water.

5. The Gram staining method of claim 1, wherein said specimens include bacterial cultures and bacterial secretions.

* * * * *